United States Patent [19]

Rosenbluth et al.

[11] Patent Number: 5,336,208

[45] Date of Patent: * Aug. 9, 1994

[54] URINARY INCONTINENCE PAD

[75] Inventors: Robert F. Rosenbluth, Laguna Niguel; Jay A. Lenker, Laguna Beach; George R. Greene, Costa Mesa; Rodney A. Brenneman, Mission Viejo; Patrick A. Maley, Laguna Niguel, all of Calif.

[73] Assignee: Advanced Surgical Intervention, Inc., San Clemente, Calif.

[*] Notice: The portion of the term of this patent subsequent to Dec. 24, 2008 has been disclaimed.

[21] Appl. No.: 810,845

[22] Filed: Dec. 20, 1991

Related U.S. Application Data

[63] Continuation-in-part of Ser. No. 639,921, Jan. 10, 1991, Pat. No. 5,074,855.

[51] Int. Cl.$^5$ .................. A61F 5/44; A61F 13/15; A61F 13/20; A61B 5/00
[52] U.S. Cl. ................... 604/329; 604/330; 604/358; 604/385.1; 604/387; 128/761
[58] Field of Search .............. 604/358, 360, 365, 369, 604/385.1, 386, 387, 389, 327, 331, 347, 352, 329, 330; 128/761

[56] References Cited

U.S. PATENT DOCUMENTS

| | | | |
|---|---|---|---|
| 3,340,876 | 9/1967 | Hill | 128/295 |
| 3,512,185 | 11/1967 | Ellis | 4/110 |
| 3,528,422 | 9/1970 | Hodas | 128/290 |
| 3,661,155 | 5/1972 | Lindan | 128/295 |
| 3,726,277 | 4/1973 | Hirschman | 604/385.1 X |
| 3,857,394 | 12/1974 | Alenany | 128/260 |
| 3,983,873 | 10/1976 | Hirschman | 128/285 |
| 4,046,147 | 9/1977 | Berg | 128/290 |
| 4,198,979 | 4/1980 | Cooney et al. | 128/295 |
| 4,209,009 | 6/1980 | Hennig | 128/1 |
| 4,421,511 | 12/1983 | Steer et al. | 604/329 |
| 4,457,314 | 7/1984 | Knowles | 128/760 |
| 4,484,917 | 11/1984 | Blackmon | 604/327 |
| 4,496,355 | 1/1985 | Hall et al. | 604/327 |
| 4,563,183 | 1/1986 | Barrodale et al. | 604/329 |
| 4,593,053 | 6/1986 | Jevne et al. | 523/111 |
| 4,595,392 | 6/1986 | Johnson et al. | 604/385 |
| 4,627,848 | 12/1986 | Lassen et al. | 604/370 |
| 4,631,062 | 12/1986 | Lassen et al. | 604/385 |
| 4,673,403 | 6/1987 | Lassen et al. | 604/385 |
| 4,690,677 | 9/1987 | Erb | 604/329 |
| 4,795,449 | 1/1989 | Schneider et al. | 604/329 |
| 4,804,380 | 2/1989 | Lassen et al. | 604/385 |
| 4,822,347 | 4/1989 | MacDougall | 604/329 |
| 4,846,819 | 7/1989 | Welch | 604/329 |
| 4,846,824 | 6/1989 | Lassen et al. | 604/385 |
| 4,979,947 | 12/1990 | Berman | 604/369 |
| 4,990,338 | 2/1991 | Blank et al. | 424/443 |
| 5,057,096 | 10/1991 | Faglione | 604/385.1 |
| 5,074,855 | 12/1991 | Rosenbluth et al. | 604/385.1 |

FOREIGN PATENT DOCUMENTS 754481 8/1956 United Kingdom .................. 81/2

Primary Examiner—Randall L. Green
Assistant Examiner—Elizabeth M. Burke
Attorney, Agent, or Firm—Klein & Szekeres

[57] ABSTRACT

A device for managing urinary incontinence in a human female includes a resilient body resilient adapted to fit between the labia minora and the floor of the vestibule of the vulva, thereby occluding the urethral meatus. An adhesive is applied to the body to provide a sealing engagement with the urethral meatus. In a first embodiment, the body has a base that seats against the floor of the vestibule, and a pair of flexible, lateral flaps that engage the labia minora. A layer of adhesive is applied to the base. A layer of highly-absorbant, hydrophilic material may be situated between the base and the adhesive layer, and/or a layer of scrim material may be so situated. The body may have a longitudinal ridge with a posterior edge having a finger hole to facilitate installation and removal of the device. In a second embodiment, the body is substantially tubular, with the adhesive applied to the exterior surface of the body. In the first and second embodiments, the body is preferably formed of a biodegradable material. In a third embodiment, the body is a flexible bladder or sac, filled with a suitable liquid or gel, that conformingly fits between the labia minora and the floor of the vestibule so as to occlude the urethral meatus. The exterior surface of the bladder is coated with an adhesive to provide a sealing engagement with the meatus. In all embodiments, the preferred adhesive is a mixture of poly 2-hydroxyethyl methacrylate and polyethylene glycol.

45 Claims, 3 Drawing Sheets

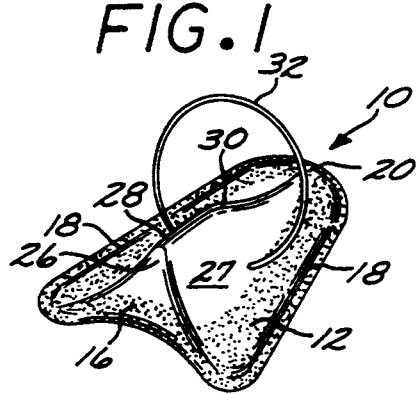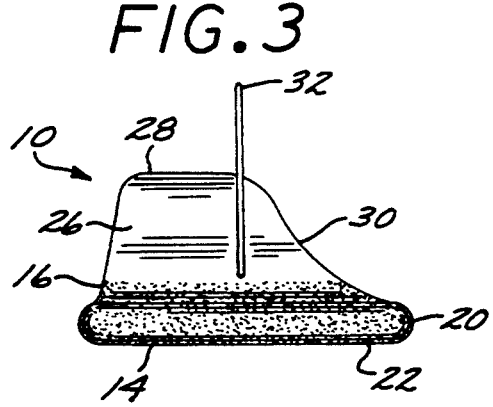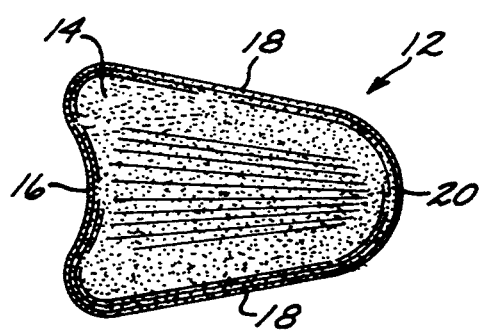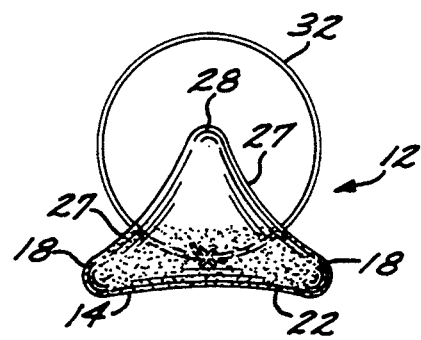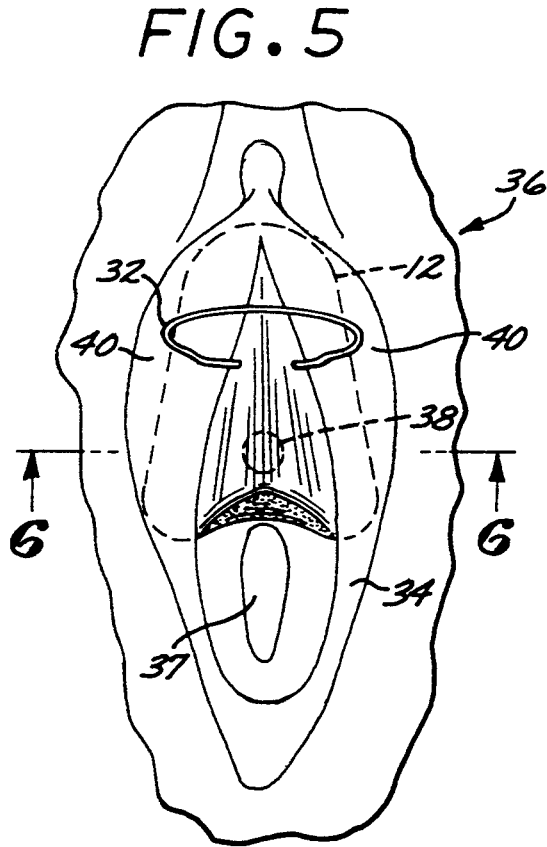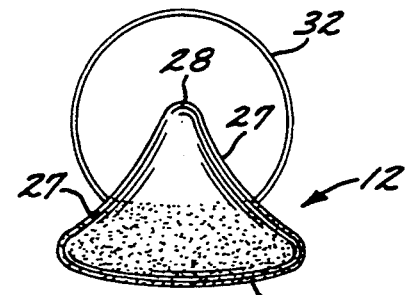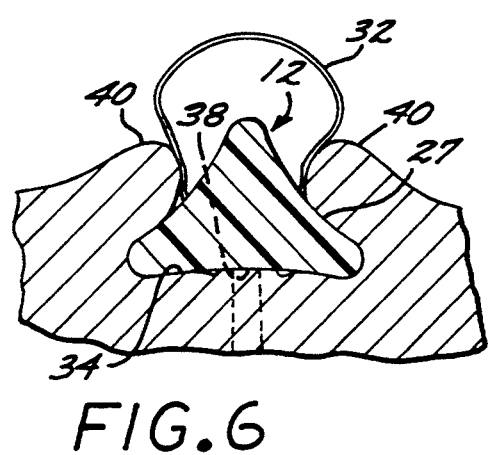

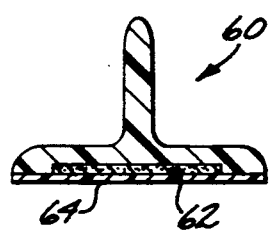
FIG. 17
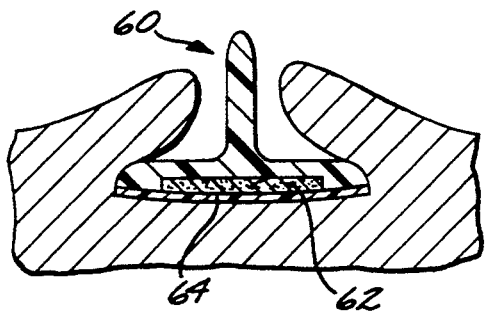
FIG. 18
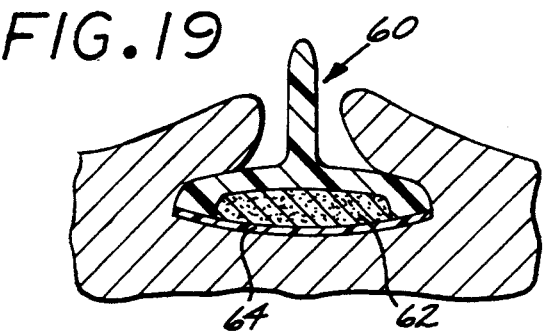
FIG. 19
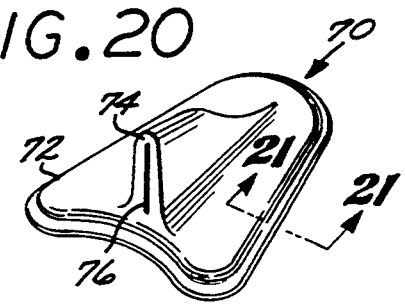
FIG. 20
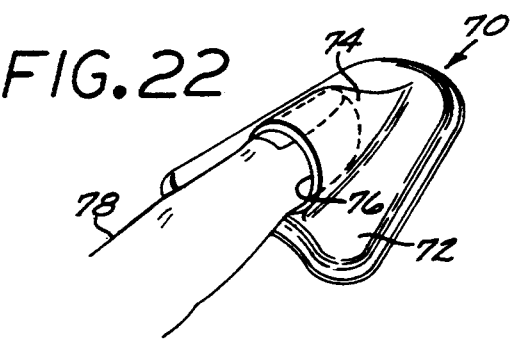
FIG. 22
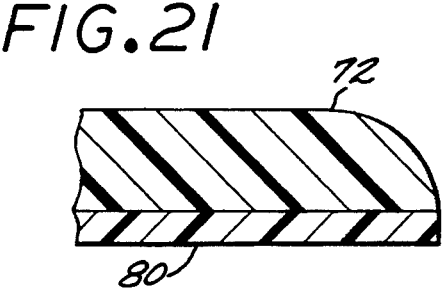
FIG. 21
FIG. 23
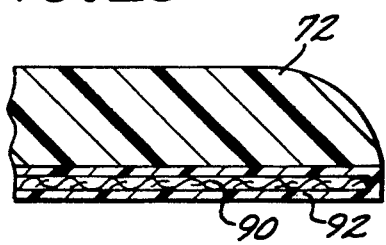
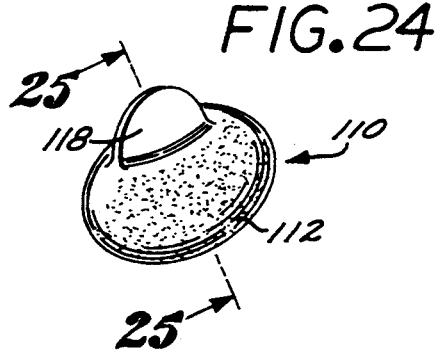
FIG. 24
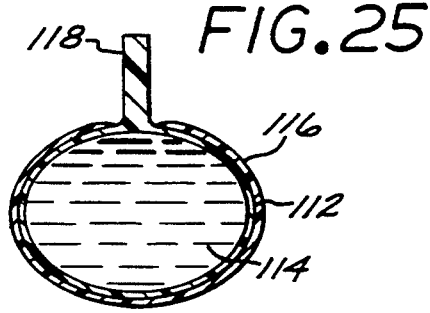
FIG. 25

URINARY INCONTINENCE PAD

CROSS-REFERENCE TO RELATED APPLICATION

This application is a Continuation-In-Part of co-pending application Ser. No. 07/639,921; filed Jan. 10, 1991: issuing as U.S. Pat. No. 5,074,855.

BACKGROUND OF THE INVENTION

This invention relates to the field of devices or appliances used to relieve or mitigate the problems associated with human urinary incontinence. More specifically, the present invention relates to a removable external closure for the human female urethra.

Urinary incontinence, due to disease, injury, or other causes, is a troublesome problem for many individuals. Surgical intervention is often required to treat severe cases of incontinence, but in those cases where the patient suffers from only a partial loss of bladder control, or where the patient is otherwise a poor candidate for surgery, nonsurgical treatment is called for. Such nonsurgical approaches are particularly appropriate for female patients who suffer from the partial, sporadic loss of bladder control sometimes referred to as "stress incontinence" or "urge incontinence". Such stress or urge incontinence, in fact, is the most common cause of urine loss in adult women.

Nonsurgical management of female urinary incontinence includes non-therapeutic management, wherein the patient wears an appliance or device proximate the urethral orifice ("meatus") that collects or captures urinary discharge. Such devices fall generally into two categories: (1) urine collection devices, and (2) absorbent pads.

Urine collection devices typically comprise a receiving orifice or receptacle for capturing urine flowing from the urethra; retention means, associated with the receptacle or orifice, for holding the receptacle or orifice in the proximity of the urethral meatus; and means for directing urine from the receptacle or orifice to a reservoir or a container or the like for disposal. Devices of this general description are disclosed in the following U.S. Pat. Nos.: 3,512,185—Ellis; 3,661,155—Lindan; 4,412,511—Steer et al.; 4,457,314—Knowles; 4,484,917—Blackmon; 4,690,677—Erb; 4,822,347—MacDougall; and 4,846,819—Welch. A variation on the urinary collection device theme is the "female external catheter", disclosed in U.S. Pat. No. 4,563,183—Barrodale et al., which includes a catheter tube having one end inserted into the urethra. In many of these devices, the retention means are configured so as to be inserted into the interlabial space, being retained therein by the anatomical structure of the external female genitalia. The Blackmon and MacDougall devices also use an adhesive to assist in retention.

The category of absorbent pads includes a wide variety of devices which generally comprise a body of absorbent material configured so as to be insertable into the interlabial space, and retained therein by the anatomical structure of the external female genitalia. Such devices typically resemble (and, indeed, can function as) catamenial sanitary napkins. The following U.S. Patents disclose devices that may generally be considered within this category: U.S. Pat. Nos. 3,983,873—Hirschman; 4,595,392—Johnson et al.; 4,627,848—Lassen et al.; 4,673,403—Lassen et al.; 4,743,245—Lassen et al.; 4,804,380—Lassen et al.; and 4,846,824—Lassen et al. A sanitary napkin that is configured for interlabial retention, and that could be used to capture and absorb urine flow, is disclosed in British Patent No. 754,481.

While the above-described devices are useful in certain applications, they are subject to a number of disadvantages. For example, the urine collection devices require the user to wear a reservoir or container that may be prone to overflow or spillage. Also, such devices are better suited to users who suffer from chronic or severe loss of bladder function, rather than those who suffer only from moderate stress or urge incontinence. The absorbent pads tend to be bulky, and may be uncomfortable for some users, especially when wet. Odor associated with urine collection devices is often noticeable by others, and is therefore undesireable.

Use of the prior art devices described above is based upon the assumption that the flow of urine out of the urethra cannot or should not be stopped. This assumption may not be true in many cases of stress or urge incontinence, which are transient in nature. In such cases, external occlusion of the urethral meatus may provide an adequate degree of continence for many patients, but this approach has been overlooked, at least for the most part, by the prior art.

There is, therefore, a need for a device that provides for the effective management of female stress or urge incontinence by means of the external occlusion of the urethral meatus; that is easy to use and comfortable to wear; and that provides for secure retention with good sealing qualities.

SUMMARY OF THE INVENTION

Broadly, the present invention is a urethral meatus occlusion device, comprising a resilient body, configured to engage and seal against the urethral meatus, and to be retained in place by engagement with the anatomical structure of the external female genitalia. More specifically, in one preferred embodiment, the body is a pad that includes a base, having a substantially triangular or arrowhead-shaped outline, that is adapted to seat against the vestibule of the vulva, anteriorly of the vaginal orifice, thereby occluding the urethral meatus. The lateral edges of the pad are configured to fit inside the labia minora, the engagement between the pad and the labia thereby retaining the pad firmly against the vestibule, in sealing engagement against the meatus. The side of the pad opposite the base is configured with a central longitudinal ridge that, when the pad is installed in the vestibule, extends into the interlabial space. A loop of thread may be inserted through the ridge to facilitate removal of the device, or a finger hole may be provided into the posterior of the ridge for the same purpose.

In a second preferred embodiment of the invention, the pad has a substantially tubular configuration, and thus lacks the lateral edges or "wings" of the first preferred embodiment. This "wingless" embodiment is adapted for use where the floor of the vestibule is narrower than what may be considered "normal". As with the first preferred embodiment, the pad seats against the floor of the vestibule, anteriorly of the vaginal orifice, thereby occluding the urethral meatus. The tubular portion of the pad is configured to fit inside the labia minora, the engagement between the pad and the labia thereby retaining the pad firmly against the vestibule, in sealing engagement against the meatus. The side of the pad opposite the base is configured with a central longitudinal ridge that, when the pad is installed in the vestibule, extends into the interlabial space, thereby facilitating insertion and removal.

In both of the aforementioned embodiments, at least that portion of the pad that lies in sealing engagement against the meatus is coated with a pressure-sensitive, hydrophilic hydrogel adhesive for retention against the vestibule. The adhesive, in concert with the resilient pad, spreads to fill the interlabial space proximate the vestibule, thereby providing a conformal fit with the anatomical structure, which enhances the retention of the device. The pad itself can be coated or impregnated with a suitable anti-bacterial or germicidal agent to inhibit infection.

In a third preferred embodiment of the invention, the body comprises an elastomeric bladder or sac, filled with a soft, compliant, biocompatible gel or liquid, and coated with a pressure-sensitive hydrophilic hydrogel adhesive, to enhance retention. The gel-filled sac spreads within the interlabial space to conform closely to the anatomic structure of the external female genitalia, and thereby seals against the urethral meatus, with the aid of the adhesive.

It will be appreciated that the present invention offers a new and advantageous approach to the management of stress and urge incontinence. For example, the device is small, unobtrusive, easy to use, and comfortable wear. By allowing the user effectively to retain urine, the device avoids the problems associated with prior art devices, enumerated above, that allow the discharge of urine. The device can be made in a variety of sizes and shapes for optimal fit for each individual user. The device is economical to manufacture, and can, therefore, be a disposable item.

These and other advantages will be better appreciated from the detailed description that follows.

BRIEF DESCRIPTION OF THE DRAWINGS

FIG. 1 is a perspective view of a female urinary incontinence device, in accordance with a first preferred embodiment of the invention;

FIG. 2 is a bottom plan view of the device of FIG. 1;

FIG. 3 is a side elevational view of the device of FIG. 1;

FIG. 4 is an anterior elevational view of the device of FIG. 1;

FIG. 5 is plan view of the device of FIG. 1, showing the device installed in the external genitalia of a human female;

FIG. 6 is a cross-sectional view taken along line 6—6 of FIG. 5;

FIG. 7 is an anterior elevational view of a first modified form of the first preferred embodiment of the device;

FIG. 17 is a cross-sectional view of a fourth modification of the first preferred embodiment, wherein the pad includes a layer of super-absorbant material;

FIG. 18 is a cross-sectional view, similar to that of FIG. 17, showing the invention as installed in the external genitalia of a human female;

FIG. 19 is a cross-sectional view, similar to that of FIG. 18, showing the super-absorbant material after it has absorbed moisture;

FIG. 20 is a perspective view of a fifth modified form of the first preferred embodiment, which includes a finger hole;

FIG. 21 is a cross-sectional view, taken along Line 21—21 of FIG. 20;

FIG. 22 is a perspective view, similar to that of FIG. 20, showing the device with a human finger inserted into the finger hole;

FIG. 23 is a cross-sectional view, similar to that of FIG. 21, showing a sixth modification of the first preferred embodiment;

FIG. 24 is a perspective view of a third preferred embodiment of the invention; and FIG. 25 is a cross-sectional view taken along Line 25—25 of FIG. 24.

DETAILED DESCRIPTION OF THE INVENTION

Figure 8:
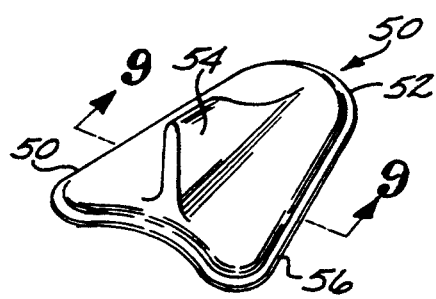
FIG. 8 is a perspective view of a second modified form of the first preferred embodiment.

Referring first to FIGS. 1 through 4 of the drawings, a female urinary incontinence device 10, in accordance with a first preferred embodiment of the present invention, is shown. The device comprises a body or pad 12, formed of a resilient foam material that is biocompatible. One suitable class of materials is that of foams formed from the water actuation of prepolymers based on either toluene diisocyanate (TDI) or methylene diphenyl diisocyanate (MDI). Such prepolymers are marketed by W. R. Grace & Co.-Conn., Organic Chemicals Division, Lexington, Mass., under the trademarks "HYPOL" (TDI) and "HYPOL PLUS" (MDI).

Alternatively, the pad 12 can be made of a biodegradable material, such as a cellulose or cotton fiber. A polyurethane foam can also be used, being rendered biodegradable by hydrolysis of a weak backbone link, such as an amine group. Other foam materials, such as polyolefins, can be used and made hydrolytically biodegradable by using weak links such as starches in the polymer backbones.

The pad 12 includes a base 14 that has the general outline of a blunt arrowhead, as shown in FIG. 2. In the first preferred embodiment of the invention, the base may be slightly concave, as shown in FIG. 4. Alternatively, the base 14 can be made slightly convex, as shown in FIG. 7, for those users who might find such a configuration more comfortable to wear. The base 14 has a concave posterior end 16, with lateral edges 18 that taper slightly toward each other as they extend toward a rounded anterior end 20. The anterior end 20 is thus somewhat narrower than the posterior end 16.

The pad is provided with an adhesive surface for retention against the floor of the vestibule. In this embodiment of the invention, the base is coated with an adhesive layer 22, comprising a pressure-sensitive, hydrophilic hydrogel adhesive material. Such hydrogel adhesives are marketed by Promeon Division of Medtronic, Inc., of Minneapolis, Minn., under the trademark "PROMEON". A detailed description of such a hydrogel composition is contained in U.S. Pat. No. 4,593,053—Jevne et al., the disclosure of which is incorporated herein by reference.

Another type of adhesive that has shown good results is a mixture of poly 2-hydroxyethyl methacrylate (PHEMA) and polyethylene glycol (PEG) as a plasticizer. The percentage of PHEMA may range from about 45% to about 75%, with a corresponding range of PEG of about 55% to about 25%. The preferred composition is about 53% to 54% PHEMA and about 47% to 46% PEG. Lower percentages of PHEMA yield greater adhesiveness, while higher percentages of PHEMA yield greater durability. The PEG has a molecular weight between about 400 and about 1000, with 400 preferred. The PHEMA is preferably a mixture of low molecular weight PHEMA (Mw between about 10,000 and about 100,000) and high molecular weight PHEMA (Mw greater than about 100,000). The low Mw PHEMA provides adhesive properties, while the high Mw PHEMA improves adhesive structural integrity. The PHEMA mixture is between about 10%–50% low Mw PHEMA and between about 90% and 50% high Mw PHEMA, with the precise mixture being determined by the particular adhesive properties desired.

While the preferred plasticizer is PEG, as described above, other plasticizers can be used, such as propylene glycol, polypropylene glycol (PPG), or glycerin.

If the pad 12 is made of TDI or MDI, the material of the pad itself can be rendered adhesive by combining the TDI or MDI one-to-one by weight with about 0.25 to 0.50 molar ammonium hydroxide during the water actuation of the foam. The resulting material has a surface that is positively charged, so that it will adhere to a negatively-charged mucoid surface (such as the surface of the vestibule and the inner portions of the labia minora).

Alternatively, the entire pad can be formed of an adhesive, such as the PHEMA/PEG mixture described above.

The side of the pad 12 opposite the base 14 includes a central longitudinal stiffening ridge 26 which forms the thickest part of the pad 12. If one adopts the convention that the base is the "bottom" of the pad 12, then the pad can be defined as having a surface 27 opposite the base that slopes "downwardly" from either side of the ridge 26 toward the edges 18, so that there is a gradual reduction in pad thickness from the ridge to the edges. Viewed another way, the pad can be defined as having a cross-sectional shape that narrows from the base 14 to the "top" or apex 28 of the ridge 26. The resulting configuration is such that a lateral cross section of the pad, taken through the ridge 26, produces a shape resembling a triangle with rounded corners and slightly concave sides, as shown in FIG. 6. Similarly, the ridge 26 has an anterior edge 30 that tapers "downwardly" from the apex 28 toward anterior end 20 of the pad 12, as shown in FIG. 3, so that the anterior end 20 of the pad 12 is substantially reduced in thickness as compared to the posterior end 16.

The device 10 is advantageously provided with a handle or tab that is either integrally molded with the pad 12, or subsequently attached to it. In the first preferred embodiment, handle is a ring or loop 32, preferably of thread, that is inserted laterally through the pad 12. The loop is preferably located near the anterior edge 28 of the ridge 26, although the precise location of the loop 32 is not critical to its function, as will be described below.

FIGS. 5 and 6 show the incontinence device 10 installed in the external genitalia of a human female. The device 10 is installed so that the base 14 is seated against the vestibule 34 of the vulva 36, anteriorly of the vaginal orifice 37, thereby occluding the urethral meatus 38. The adhesive surface seals the meatus sufficiently to prevent the escape of urine. The lateral edges 18 and the anterior end 20 of the pad are tucked under the labia minora 40. The engagement between the labia minora and the sloping surface 27 enhances the retention of the pad 12 in engagement with the vestibule 34. The concavity in the posterior end 16 of the pad 12 allows for somewhat greater surface area for engagement by the labia minora, while leaving a clearance for the vaginal opening 37. The ridge 26 extends into the interlabial space, and the loop 32 protrudes from between the labia majora (not shown), so as to be exposed to facilitate manual grasping, for removal of the device.

The pad 12 can be provided in a number of sizes to fit a large variety of individuals. The length of the pad should be approximately the same as the distance between the anterior lip of the vaginal orifice and the juncture of the labia minora. The width of the pad should optimally conform substantially to the width of the vestibule. Predetermined sizes can be trimmed individually for optimum fit. In some cases, a mold of the relevant portions of the vulva may be taken prior to sizing the pad.

The adhesive layer 22 not only provides a fluid-tight seal for the urethral meatus, but it also minimizes slippage of the device. The central ridge 26 lends rigidity that resists deformation of the pad and rupture of the adhesive layer under fluid pressure from the urethra, thereby enhancing the fluid-tight seal provided by the pad against the urethral meatus. It may be advantageous to extend the adhesive layer onto the labia-engaging surface 27, thereby further enhancing the stability of the device.

An incontinence device constructed in accordance with the first preferred embodiment of the invention, as described above, can be made to withstand short-term fluid pressures from the urethra in the range of up to at least about 100, and preferably to about 170, centimeters of water without significant leakage. Pressures in this range are those that would typically result in involuntary urine voiding in cases of stress and urge incontinence, with 170 centimeters of water being the approximate maximum bear-down pressure for a typical adult human female.

As an option, the foam material of the pad, and/or the adhesive surface, can be provided with a medically-active composition. An antibacterial or germicidal agent, such as silver oxide or silver azide may be used, for example.

Figure 9:
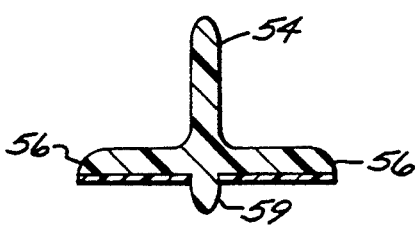
FIG. 9 is cross-sectional view taken along Line 9—9 of FIG. 8.
Figure 10:
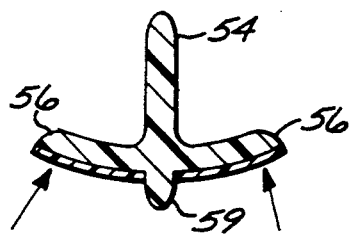
FIG. 10 is a cross-sectional view, similar to that of FIG. 9, showing the flexing of the lateral edges of the pad.

The first preferred embodiment lends itself to several modifications that may provide better comfort for certain individuals. For example. FIGS. 8, 9, and 10 show a modified device 50, which includes a pad 52 of substantially uniform thickness, except for a longitudinal ridge 54. This modification provides lateral flaps 56 that flex more easily than those of the embodiment of FIGS.

Figure 11:
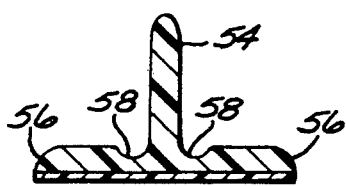
FIG. 11 is a cross-sectional view of a third modified form of the first preferred embodiment.
Figure 12:
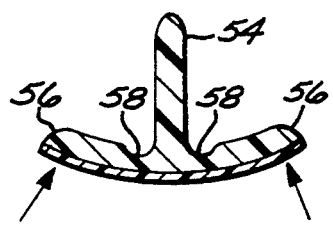
FIG. 12 is a cross-sectional view, similar to that of FIG. 11, showing the flexing of the lateral edges of the pad.

1-7 when engaged against the labia minora, thereby yielding a better conformal fit with the genitalia. Still greater flexibility may be provided by forming a longitudinal groove 58 in each of the flaps 56, on either side of the ridge 54, as shown in FIGS. 11 and 12.

As still another option, a short protuberance 59 may be provided on the base, as shown in FIGS. 9 and 10. The protuberance 59 is dimensioned to be received wholly or partially within the urethral meatus, thereby facilitating proper placement of the device, and enhancing the occlusion of the meatus.

Another modification of the first preferred embodiment is shown in FIGS. 17, 18, and 19. As shown in these figures a modified device 60 includes a layer 62 of highly-absorbant hydrophilic material adjacent the adhesive layer 64 on the base of the pad. The hydrophilic layer 62 is preferably a mixture of the PHEMA/PEG adhesive and either a microsponge material, such as carboxymethylcellulose (CMC) or a super-absorbant material, such as potassium polyacrylate. The hydrophilic layer 62 draws moisture from the adhesive layer 64 and absorbs the moisture, thereby prolonging the useful lifetime of the adhesive by delaying saturation. Absorption of moisture causes the hydrophilic layer 62 to swell, as shown in FIG. 19, which may enhance the sealing properties of the device.

Still another modification of the first preferred embodiment is shown in FIGS. 20, 21 and 22. In these figures, a modified device 70 has a a pad 72 having an integral longitudinal ridge 74. The ridge 74 a finger hole 76 in its posterior edge. The finger hole 76 is normally in a collapsed state, as shown in FIG. 20. It expands to receive the user's finger 78, as shown in FIG. 22, to facilitate installation and removal.

In FIG. 21, the device 70 is shown as having an adhesive layer 80 applied directly to the base of the pad 72, as previously described. FIG. 23 shows still another feature that can be incorporated, as a further modification, into any of the previously-described variations of the first preferred embodiment. In this variation or modification, a scrim layer 90 is enclosed within the adhesive 92 applied to the base of the pad. The scrim layer 90 is preferably a thin, non-woven sheet of polyester that can reinforce an elastomeric material. In the present invention, the scrim layer 90 adds structural integrity to the adhesive material, thereby enhancing the durability of the device. As shown in FIG. 23, the scrim layer 90 is placed in the adhesive before the adhesive is cured to a semi-solid. Alternatively, the scrim layer 90 can be applied to the base of the pad before the adhesive is applied, in which case the scrim layer would be sandwiched between the adhesive and the base of the pad.

Figure 13:
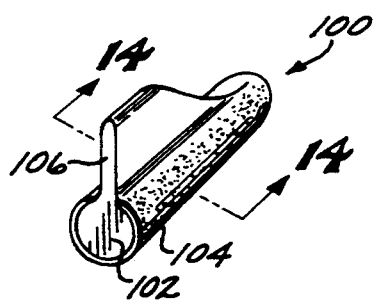
FIG. 13 is a perspective view of a second preferred embodiment of the invention.
Figure 14:
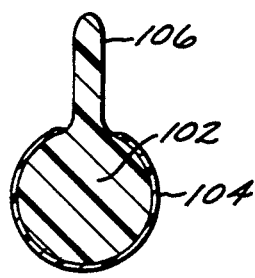
FIG. 14 is a cross-sectional view taken along Line 14—14 of FIG. 13.
Figure 15:
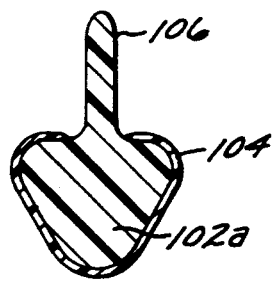
FIG. 15 is a cross-sectional view, similar to that of FIG. 14, showing a modified form of the second preferred embodiment.
Figure 16:
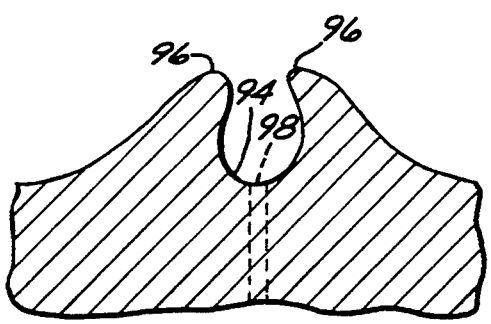
FIG. 16 is a cross-sectional view of the external female genitalia, showing a vestibule of the configuration for which the second preferred embodiment is adapted.

It has been noted that some potential users of the present invention have a relatively narrow vestibule floor. This type of anatomical structure is shown in FIG. 16, which shows a simplified cross-sectional view of external female genitalia, wherein the vestibule floor 94 and the labia minora 96 define a relatively narrow space proximate the urethral meatus 98. For those with this type of anatomical structure, the above-described first preferred embodiment may be uncomfortable, or altogether unsuitable. Consequently, a second preferred embodiment, illustrated in FIGS. 13, 14, and 15, is contemplated for such users.

In accordance with this second preferred embodiment, a female urinary incontinence device 100 includes substantially tubular pad 102, substantially the entire exterior surface of which is coated with an adhesive 104, of a type described above. The pad 102 has a longitudinal ridge 106, preferably not coated with the adhesive, that is used as a gripping element to facilitate installation and removal. As shown in FIGS. 13 and 14, the tubular pad may have a substantially elliptical cross-section. Alternatively, as shown in FIG. 15, a pad 102a, having a cross-sectional shape similar to a rounded triangle, may be more suitable for some users. Optionally, a protuberance (not shown), such as the protuberance 59 shown in FIGS. 9 and 10 and described above, can be provided on this embodiment to facilitate proper placement and to enhance occlusion.

FIGS. 24 and 25 illustrate a third preferred embodiment of the invention. A urinary incontinence device 110, in accordance with this embodiment, includes a thin, flexible sac or bladder 112, formed of polyurethane or a similar thin, resilient, flexible material. The sac 112 is filled with a suitable biocompatible liquid or gel 114 by means of a needle, and the needle hole is then sealed, thereby forming a compliant sac. A preferred material for filling the sac is a hydrogel, similar the hydrogel adhesives described above. Substantially the entire exterior surface of the sac is coated with an adhesive 116, of a type described above.

In use, the device 110 is inserted under the labia minora so as to be seated against the floor of the vestibule, occluding the urethral meatus. The sac conforms to the anatomical structure of the external female genitalia, filling the interlabial space, and sealing against the urethral meatus with the aid of the adhesive. Because the sac is so compliant, it can be used for a wide variety of anatomical structures, providing high levels of comfort. The device may advantageously be provided with a raised tab 118, not coated with the adhesive, to be gripped by the user, to facilitate the installation and removal of the device 110.

From the foregoing, the advantages of the present invention will be readily appreciated. The incontinence device in accordance with the present invention provides effective management of female urinary incontinence, especially stress and urge incontinence, without the inconvenience and discomfort associated with prior art urine collection devices and absorbent pads. The present invention is easy to use and comfortable to wear. It is easily shaped and sized to fit each individual user's anatomy with optimum effectiveness and comfort. Easily and inexpensively manufactured, the present invention can be made as a disposable item.

While several preferred embodiments and modifications thereof have been described above, it should be understood that still further modifications and variations will suggest themselves to those skilled in the pertinent arts. Such variations and modifications should be considered within the spirit and scope of the invention, as defined in the claims that follow.

What is claimed is:

1. An incontinence device for managing urinary incontinence in a human female having external genitalia that include a vulva with a vestibule floor and a pair of labia minora, and having a urethral meatus between the labia minora, comprising:

a body of biocompatible material configured to fit between the labia minora and the vestibule floor, said body having surface means for occlude the urethral meatus;

said surface means having a vestibule floor-contacting surface on the body; and adhesive means on the vestibule floor-contacting surface for providing a sealing engagement between the body and the urethral meatus.

2. The device of claim 1, wherein the vestibule floor-contacting surface includes a base that seats against the vestibule floor and wherein the body includes a pair of lateral flaps that engage the labia minora, the lateral flaps being configured so as to allow a substantial amount of flexing to conform to the configuration of the external genitalia.

3. The device of claim 2, wherein each of the lateral flaps has flexibility and a longitudinal groove that increases the flexibility of the lateral flaps.

4. The device of claim 1, wherein the body has a surface opposite the vestibule floor-contacting surface that includes a longitudinal ridge.

5. The device of claim 4, wherein the longitudinal ridge has a posterior edge with a hole adapted to receive a human finger.

6. The device of claim 4, wherein the body is substantially tubular.

7. The device of claim 6, wherein the body has a substantially elliptical cross-section.

8. The device of claim 6, wherein the body has a cross-section that is substantially a rounded triangle.

9. The device of claim 1, wherein the vestibule floor-contacting surface includes a base that seats against the vestibule floor, and wherein the body includes a pair of flaps that engage the labia minora, and wherein the adhesive means includes a layer of adhesive material applied to the base, the device further comprising:

a layer of highly-absorbant, hydrophilic material in the base and adjacent to the layer of adhesive material.

10. The device of claim 9, wherein the hydrophilic material includes potassium polyacrylate.

11. The device of claim 9, wherein the hydrophilic material includes carboxymethylcellulose.

12. The device of claim 9, wherein the hydrophilic material is a mixture of adhesive material and a material selected from a group consisting of carboxymethylcellulose and potassium polyacrylate.

13. The device of claim 1, wherein the body is substantially made of a biodegradable material.

14. The device of claim 13, wherein the biodegradable material is selected from a group consisting of cotton fiber, cellulose fiber, and a biodegradable polymeric foam.

15. The device of claim 1, wherein the adhesive means includes a hydrogel adhesive comprising a mixture of poly 2-hydroxyethyl methacrylate and a plasticizer.

16. The device of claim 15, wherein the plasticizer is selected from a group consisting of polyethylene glycol, propylene glycol, polypropylene glycol, and glycerin.

17. The device of claim 1, wherein the body comprises a sac having an exterior surface and an interior filled with a biocompatible liquid or gel material, and wherein the adhesive means includes a coating of adhesive material on the exterior surface of the sac.

18. The device of claim 1, wherein the vestibule floor-contacting surface includes a base that seats against the vestibule floor and wherein the body includes a pair of lateral flaps that engage the labia minora, and wherein the adhesive means includes a layer of adhesive material applied to the base, the device further comprising:

a layer of scrim material contained within the layer of adhesive material.

19. The device of claim 18, wherein the scrim material includes a thin sheet formed substantially from a polyester.

20. The device of claim 1, further comprising:

a protuberance on the body dimensioned to be received at least partially within the urethral meatus.

21. The device of claim 1, wherein the body and the adhesive means are formed substantially of a hydrogel comprising a mixture of poly 2-hydroxyethyl methacrylate and a plasticizer selected from a group consisting of polyethylene glycol, polypropylene glycol, propylene glycol, and glycerin.

22. An incontinence device for managing urinary incontinence in a human female having external genitalia that include a vulva with a vestibule floor and a pair of labia minora, and having a urethral meatus between the labia minora, comprising:

a body dimensioned and shaped for fitting between the labia minora and the vestibule, said body having surface means for occluding the urethral meatus, said surface means including a vestibule floor-contacting base and adhesive means on the base for sealing against the urethral meatus, the body being retained in place against the urethral meatus substantially by adhesion to the vestibule floor, wherein the body includes a pair of lateral flaps configured to engage the labia minora with a substantial amount of flexing so as to conform to the configuration of the external genitalia.

23. The device of claim 22, wherein each of the lateral flaps has flexibility and includes a longitudinal groove that increases the flexibility of the flaps.

24. The device of claim 22, wherein the base includes a protuberance dimensioned to be received at least partially within the urethral meatus.

25. The device of claim 22, wherein the body is made of a biodegradable material selected from a group consisting of cotton fiber, cellulose fiber, and biodegradable polymeric foam.

26. The device of claim 22, wherein the adhesive means includes a hydrogel adhesive comprising a mixture of poly 2-hydroxyethyl methacrylate and a plasticizer selected from a group consisting of polyethylene glycol, polypropylene glycol, propylene glycol, and glycerin.

27. An incontinence device for managing urinary incontinence in a human female having external genitalia that include a vulva with a vestibule floor and a pair of labia minora, and having a urethral meatus between the labia minora, comprising:

a body dimensioned and shaped for fitting between the labia minora and the vestibule, said body having surface means for occluding the urethral meatus, said surface means including a base and adhesive means on the base for sealing against the urethral meatus, the body being retained in place against the urethral meatus substantially by adhesion to the vestibule floor, the body including a longitudinal ridge with a posterior edge having a hole configured to receive a human finger.

28. The device of claim 27, wherein the body is made of a biodegradable material selected from a group consisting of cotton fiber, cellulose fiber, and biodegradable polymeric foam.

29. The device of claim 27, wherein the adhesive means includes a hydrogel adhesive comprising a mixture of poly 2-hydroxyethyl methacrylate and a plasticizer selected from a group consisting of polyethylene glycol, polypropylene glycol, propylene glycol, and glycerin.

30. An incontinence device for managing urinary incontinence in a human female having external genitalia that include a vulva with a vestibule floor and a pair of labia minora, and having a urethral meatus between the labia minora, comprising:

a substantially tubular body of resilient material configured to fit between the labia minora and the vestibule floor, said body having surface means for occluding the urethral meatus;

said surface means comprising a vestibule floor-contacting surface on the body; and adhesive means on the vestibule floor-contacting surface for providing a sealing engagement between the body and the urethral meatus.

31. The device of claim 30, wherein the body has a surface opposite the vestibule floor-contacting surface that includes a longitudinal ridge.

32. The device of claim 30, wherein the body is made of a biodegradable material selected from a group consisting of cotton fiber, cellulose fiber, and biodegradable polymeric foam.

33. The device of claim 30, wherein the adhesive means includes a hydrogel adhesive comprising a mixture of poly 2-hydroxyethyl methacrylate and a plasticizer selected from a group consisting of polyethylene glycol, polypropylene glycol, propylene glycol, and glycerin.

34. An incontinence device for managing urinary incontinence in a human female having external genitalia that include a vulva with a vestibule floor and a pair of labia minora, and having a urethral meatus between the labia minora, comprising:

a body dimensioned and shaped for fitting between the labia minora and the vestibule, said body having surface means for occluding the urethral meatus, said surface means including a base and adhesive means on the base for sealing against and the urethral meatus, the body being retained in place against the urethral meatus substantially by adhesion to the vestibule floor, wherein the adhesive means includes a layer of adhesive material applied to the base, the device further comprising:

a layer of highly-absorbant, hydrophilic material in the base and adjacent to the layer of adhesive material.

35. The device of claim 34, wherein the hydrophilic material includes potassium polyacrylate.

36. The device of claim 34, wherein the hydrophilic material includes carboxymethylcellulose.

37. The device of claim 34, wherein the hydrophilic material is a mixture of adhesive material and microsponge material selected from a group consisting of carboxymethylcellulose and potassium polyacrylate.

38. The device of claim 34, wherein the body is made of a biodegradable material selected from a group consisting of cotton fiber, cellulose fiber, and biodegradable polymeric foam.

39. The device of claim 34, wherein the adhesive means includes a hydrogel adhesive comprising a mixture of poly 2-hydroxyethyl methacrylate and a plasticizer selected from a group consisting of polyethylene glycol, polypropylene glycol, propylene glycol, and glycerin.

40. An incontinence device for managing urinary incontinence in a human female having external genitalia that include a vulva with a vestibule floor and a pair of labia minora, and having a urethral meatus between the labia minora, comprising:

a body dimensioned and shaped for fitting between the labia minora and the vestibule, said body having surface means for occluding the urethral meatus, said surface means including a base and adhesive means on the base for sealing against the urethral meatus, the body being retained in place against the urethral meatus substantially by adhesion to the vestibule floor, wherein the adhesive means includes a layer of adhesive material applied to the base, the device further comprising:

a layer of scrim material contained within the layer of adhesive material.

41. The device of claim 40, wherein the scrim material includes a thin sheet formed substantially from a polyester.

42. The device of claim 40, wherein the body is made of a biodegradable material selected from a group consisting of cotton fiber, cellulose fiber, and biodegradable polymeric foam.

43. The device of claim 40, wherein the adhesive means includes a hydrogel adhesive comprising a mixture of poly 2-hydroxyethyl methacrylate and a plasticizer selected from a group consisting of polyethylene glycol, polypropylene glycol, propylene glycol, and glycerin.

44. An incontinence device for managing urinary incontinence in a human female having external genitalia that include a vulva with a vestibule floor and a pair of labia minora, and having a urethral meatus between the labia minora, comprising:

a sac having an exterior surface means for occluding the urethral meatus and an interior filled with a biocompatible liquid or gel material, said sac configured to fit conformingly between the labia minora and the vestibule floor, thereby occluding the urethral meatus; and adhesive means on the exterior surface means of the sac for providing a sealing engagement between the sac and the urethral meatus.

45. The device of claim 44, wherein the adhesive means includes a hydrogel adhesive comprising a mixture of poly 2-hydroxyethyl methacrylate and a plasticizer selected from a group consisting of polyethylene glycol, polypropylene glycol, propylene glycol, and glycerin.

* * * * *